United States Patent [19]

Webb et al.

[11] Patent Number: 5,004,700
[45] Date of Patent: Apr. 2, 1991

[54] HUMIDITY SENSOR

[75] Inventors: Brian C. Webb, Sunbury-on-Thames; Derek G. Pedley, Amersham; Stephen J. Prosser, Thame, all of United Kingdom; Masaya Hijikigawa; Hisatoshi Furubayashi, both of Yamatokoriyama, Japan

[73] Assignees: EMI Limited, Hayes, United Kingdom; Sharp Kabushiki Kaisha, Osaka, Japan

[21] Appl. No.: 561,377

[22] Filed: Aug. 1, 1990

Related U.S. Application Data

[60] Division of Ser. No. 237,693, Aug. 26, 1988, abandoned, which is a continuation of Ser. No. 641,693, Aug. 17, 1984, abandoned.

[30] Foreign Application Priority Data

Aug. 19, 1983 [GB] United Kingdom ............... 8322418

[51] Int. Cl.$^5$ ................... H01L 21/288; G01N 27/12
[52] U.S. Cl. ........................ 437/42; 437/40; 437/228; 437/231; 437/235; 437/7; 357/25; 338/34; 338/35; 430/311
[58] Field of Search .............. 437/7, 40, 42, 228, 437/231, 235; 357/25; 338/34, 35; 427/412.1, 58; 430/311; 428/411.1; 525/60, 61

[56] References Cited

U.S. PATENT DOCUMENTS

| | | | |
|---|---|---|---|
| 3,715,702 | 2/1973 | Nicholas | 338/35 |
| 3,916,367 | 10/1975 | Nicholas | 338/35 |
| 3,983,527 | 9/1976 | Ohsato et al. | 338/35 |
| 4,158,807 | 6/1979 | Senturia | 357/23.14 |
| 4,263,576 | 4/1981 | Murata et al. | 338/35 |
| 4,288,775 | 9/1981 | Bennewitz et al. | 338/35 |
| 4,302,530 | 11/1981 | Zemel | 357/25 X |
| 4,326,414 | 4/1982 | Terada et al. | 338/35 |
| 4,330,718 | 5/1982 | Kinomoto et al. | 338/35 |
| 4,337,658 | 7/1982 | Motchenbacher et al. | 338/35 |
| 4,343,688 | 8/1982 | Harwood | 338/35 |
| 4,344,062 | 8/1982 | Sudoh et al. | 338/35 |
| 4,386,336 | 5/1983 | Kinomoto et al. | 338/35 |
| 4,422,129 | 12/1983 | Briant et al. | 338/35 |
| 4,424,508 | 1/1984 | Harata et al. | 338/35 |
| 4,464,647 | 8/1984 | Yokomizo | 338/35 |
| 4,486,292 | 12/1984 | Blackburn | 357/25 X |
| 4,496,931 | 1/1985 | Watanabe et al. | 338/34 |
| 4,514,263 | 4/1985 | Janata | 357/25 X |
| 4,515,653 | 5/1985 | Furubayashi et al. | 204/192.32 |
| 4,562,725 | 1/1986 | Oka et al. | 357/25 |
| 4,567,221 | 1/1986 | Maruyama et al. | 525/60 |
| 4,635,027 | 1/1987 | Miyoshi et al. | 338/35 |
| 4,638,346 | 1/1987 | Inami et al. | 338/35 |
| 4,642,601 | 2/1987 | Sugawara et al. | 338/35 |
| 4,651,121 | 3/1987 | Furubayashi et al. | 338/35 |
| 4,784,936 | 11/1988 | White et al. | 430/311 |
| 4,839,219 | 6/1989 | Uekita et al. | 428/411.1 |
| 4,900,405 | 2/1990 | Otagawa et al. | 204/153.18 |
| 4,943,471 | 7/1990 | Uekita et al. | 428/411.1 |

FOREIGN PATENT DOCUMENTS

| | | | |
|---|---|---|---|
| 52-87381 | 7/1977 | Japan | 357/25 |
| 087381 | 7/1977 | Japan | |

OTHER PUBLICATIONS

Gdula, R. A., "Composite Dielectric Layer", IBM Tech. Disc. Bull., vol. 14, No. 9, Feb. 1972, p. 2609.
Encyclopedia of Chemical Technology, John Wiley & Sons, 1982, vol. 20, pp. 210–211, vol. 3, p. 157.
"An MOS Device for AC Measurement of Surface Impedance with Application to Moisture Monitoring", Garverick et al, IEEE Transactions on Electron Devices, vol. ED-29, No. 1, Jan. 1982.

*Primary Examiner*—Olik Chaudhuri
*Assistant Examiner*—M. Wilczewski
*Attorney, Agent, or Firm*—Fleit, Jacobson, Cohn, Price, Holman & Stern

[57] ABSTRACT

A method of making a humidity sensor comprises providing a host device constituted by a semi-conductor substrate (10) and a gate insulator (13) of an insulated gate field effect transistor, forming a layer (14) of poly (vinyl alcohol) (PVA) on the exposed surface of the insulator, heat treating the layer to crystallize and stabilize the PVA, and forming a gate electrode (15) on the PVA layer, so that the gate electrode is porous allowing ambient water vapor to be absorbed by the PVA which, in response, undergoes a change of bulk dielectric constant, thereby causing a change in gate capacitance of the transistor resulting in a detectable change of electrical conductivity in the drain source channel.

13 Claims, 1 Drawing Sheet

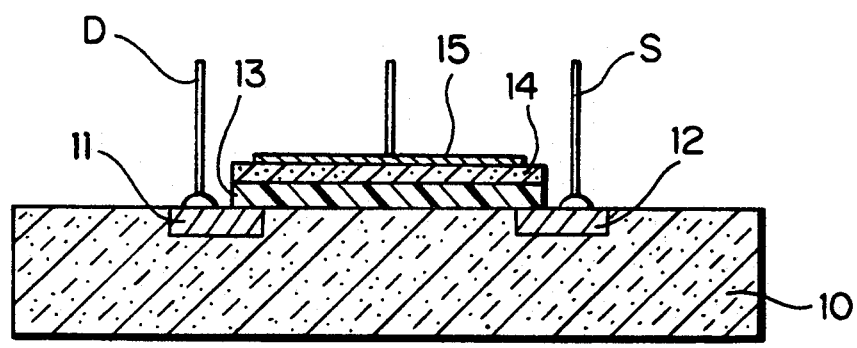

HUMIDITY SENSOR

This is a division of application Ser. No. 237,693, filed Aug. 26, 1988, now abandoned, which is a continuation of application Ser. No. 641,693, filed Aug. 17, 1984, now abandoned.

This invention relates to a method of fabricating a humidity sensor.

BACKGROUND OF THE INVENTION

Humidity sensitive capacitors are known. These devices have the disadvantage that any change of capacitance, brought about by a change of ambient water vapor partial pressure, tends to be rather small and so considerable care is needed to eliminate stray capacitance which could arise in an associated electrical circuit and would otherwise mask the effect to be detected.

BRIEF SUMMARY OF THE INVENTION

It is an object of this invention to provide a method of fabricating a different form of humidity sensor.

Accordingly, there is provided a method of fabricating a humidity sensor comprising an insulated gate field effect transistor having a layer of polyvinyl alcohol between the gate electrode and the gate insulator, the gate electrode being arrange so as to be capable of exposing said layer to ambient water vapor, wherein the layer of polyvinyl alcohol is capable of absorbing ambient water vapor to which it is exposed and, as a result of absorption, undergoes a change of bulk dielectric constant thereby to cause a detectable change of electrical conductivity in the drain source channel of the transistor.

A change of bulk dielectric constant, caused by absorption of water vapor, results in a change of gate capacitance which, for a fixed gate voltage, causes a corresponding change in drain current. The extent of the change in drain current depends on the amount of water vapor absorbed which, in turn, depends on the water vapor partial pressure. For a given sensor, therefore, the drain current can provide an indication of the water vapor partial pressure.

According to the present invention there is provided a method of fabricating a humidity sensor comprising the steps of, providing a host device constituting the semi-conductor substrate and the gate insulator of an insulated gate field effect transistor, forming a layer of an aqueous solution of polyvinyl alcohol on the exposed surface of the gate insulator, subjecting the layer to heat treatment so as to cause crystallization and/or stabilization of the polyvinyl alcohol, and forming a gate electrode on the layer, so treated.

Said layer of an aqueous solution of polyvinyl alcohol may be formed on the exposed surface of the gate insulator by spin coating. Said heat treatment may comprise heating the host device, with the layer applied, and at a temperature typically between 120° and 250°, but preferably about 180°.

BRIEF DESCRIPTION OF THE DRAWING

An embodiment of the invention is now described, by way of example only, by reference to the only drawing which shows a cross-sectional view through the sensor.

DETAILED DESCRIPTION

The humidity sensor of this invention comprises an insulated gate field effect transistor (IGFET) including, between the gate electrode and the gate insulator a layer of a hydrophilic material, polyvinyl alcohol (PVA). When this material absorbs ambient water vapor it undergoes a change of bulk dielectric constant.

As is known, if the drain voltage $V_D$ is held at a fixed value consistent with operation of the IGFET in the saturation region of the drain current—drain voltage ($I_D$–$V_D$) characteristic the drain current $I_D$ is related to the gate voltage $V_G$ by the approximate expression:

$$I_D = W/2L \; \mu C(V_G - V_T)^2$$

where W and L are respectively the width and length of the conduction channel and depend on the value of $V_D$, $\mu$ is the charge carrier mobility in the conduction channel, C is the gate capacitance and $V_T$ is the threshold voltage.

A change of bulk dielectric constant, caused by absorption of water vapor, causes a change in gate capacitance C which results in a change in drain current $I_D$. The extent of a capacitance change depends on the amount of water vapor absorbed which is a function of the ambient water vapor partial pressure. Thus, when the IGFET operates at a fixed gate voltage at AC the drain current can provide an indication of the ambient water vapor partial pressure.

Referring now to the drawing, the sensor comprises a substrate 10 of a semiconductor material, typically silicon. The substrate has a doping of one polarity type (usually p-type) and two spaced diffusion apart regions 11, 12 having a doping of the other polarity type (usually n-type). These regions consitute the drain and source and are provided with respective drain and source electrodes D, S. The gate insulator 13 is formed typically of a layer of silicon dioxide or silicon nitride and carries a further layer 14 of the hydrophilic material, polyvinyl alcohol. The gate electrode 15 is formed at the uppermost surface of layer 14 and is arranged so as to be capable of exposing the layer to ambient water vapor.

The substrate 10 having the source and drain diffusion regions 11, 12 and the gate insulator 13 constitute a host device upon which the water absorbent layer 14 is deposited. The host device is fabricated by known semiconductor techniques apparent to persons skilled in the art.

To deposit layer 14 an adhesion promoter in the form of a silane coupling reagent (e.g. 10% solution of glycidoxy propyl trimethoxysilane (GPTS) in ethanol) is applied to the substrate by spin coating so as to cover the gate insulator 13. The substrate is then dried in air, typically at 90° C. for about one hour and an aqueous solution of polyvinyl alcohol (e.g. 1 gm PVA per 5 ml H$_2$O) is applied, again by spin coating, as a layer covering the gate insulator. Spin coating may typically be at 3000 r.p.m. for 15 seconds. It has been found that if the coated substrate is subjected then to heat treatment, crystallization of the PVA occurs and this results in an absorbent layer which adheres reliably to the substrate. Typically heat treatment involves heating in nitrogen gas for about 30 minutes at 180° C.

The absorbent layer may then be patterned, as desired. To this end a layer of a photo resist is applied to the substrate, which is then positioned below a suitably configured photolithographic shadow mask. The resist is developed by exposure to UV radiation (e.g. 500 W for two minutes) and subjected to a plasma etch in an oxygen atmosphere at 0.4 torr to remove unwanted PVA. Superfluous resist, covering the remaining PVA is removed then using an organic solvent, for example methylene dichloride or acetone.

The gate electrode 15 comprises an evaporation of gold (or copper, for example) on the uppermost surface of the patterned layer 14. In order to permit exposure of layer 14 to water vapor the evaporation may be patterned either using a photolithographic technique as described in the immediately preceding paragraph or alternatively by selectively etching the evaporation using, for example, an ion beam milling technique. Alternatively, if the electrode is made thin enough it will be sufficiently porous to provide the desired degree of exposure. To this end the electrode should be typically between 100 Å and 500 Å thick, and preferably around 200 Å thick.

In operation of the sensor suitable gate and drain voltages $V_G$, $V_D$ are applied at respective electrodes and the drain current $I_D$, indicative of ambient water vapor partial pressure, is monitored. The response of a humidity sensor according to this invention is found to be particularly sensitive and reproducible. Moreover the sensor has the advantage that it is a compact, composite solid state device.

We claim:

1. A method of fabricating a humidity sensor comprising the steps of:
   providing a host device constituting a semi-conductor substrate and the gate insulator of an insulated gate field effect transistor, the gate insulator having an exposed surface;
   forming a layer of an aqueous solution of polyvinyl alcohol on the exposed surface of the gate insulator;
   subjecting said layer to heat treatment to cause crystallization and/or stabilization of the polyvinyl alcohol; and
   forming a gate electrode on said layer so treated.

2. A method as claimed in claim 1 wherein said layer forming step comprises depositing said layer of an aqueous solution of polyvinyl alcohol by spin coating.

3. A method according to claim 2 wherein said heat treatment includes heating the host device, with said layer of aqueous solution of polyvinyl alcohol applied, at a temperature in the range from 120° C. to 250° C.

4. A method according to claim 2 including patterning said layer of polyvinyl alcohol after being subjected to said heat treatment.

5. A method according to claim 2 including patterning said gate electrode thereby to expose said layer of polyvinyl alcohol to ambient water vapor.

6. The method as claimed in claim 2 wherein said spin coating comprises depositing said layer of an aqueous solution of polyvinyl alcohol in a thickness in the range from 100 Å to approximately 500 Å to expose the layer of polyvinyl alcohol to ambient water vapor.

7. The method as claimed in claim 1 wherein said layer forming step comprises:
   applying a silane coupling reagent adhesion promoter to said substrate by spin coating to cover said gate insulator;
   drying said substrate in air at approximately 90° C. for approximately one hour; and
   depositing said layer to cover said gate insulator by spin coating at substantially 300 rpm for substantially fifteen seconds.

8. A method according to claim 1 wherein said heat treatment includes heating the host device, with said layer of aqueous solution of polyvinyl alcohol applied, at a temperature in the range from 120° C. to 250° C.

9. A method according to claim 8 including patterning said layer of polyvinyl alcohol after being subjected to heat treatment.

10. A method according to claim 8 including patterning said gate electrode thereby to expose said layer of polyvinyl alcohol to ambient water vapor.

11. A method according to claim 1 including patterning said layer of polyvinyl alcohol after being subjected to said heat treatment.

12. A method according to claim 11 including patterning said gate electrode thereby to expose said layer of polyvinyl alcohol water vapor.

13. A method according to claim 1 including patterning said gate electrode thereby to expose said layer of polyvinyl alcohol to ambient water vapor.

* * * * *